United States Patent
Tao et al.

(10) Patent No.: US 9,581,561 B2
(45) Date of Patent: Feb. 28, 2017

(54) INTEGRATED OPTOELECTROCHEMICAL SENSOR FOR NITROGEN OXIDES IN GASEOUS SAMPLES

(71) Applicants: Nongjian Tao, Scottsdale, AZ (US); Erica Forzani, Mesa, AZ (US); Rodrigo A Iglesias, Tempe, AZ (US)

(72) Inventors: Nongjian Tao, Scottsdale, AZ (US); Erica Forzani, Mesa, AZ (US); Rodrigo A Iglesias, Tempe, AZ (US)

(73) Assignee: ARIZONA BOARD OF REGENTS FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 164 days.

(21) Appl. No.: 14/160,035

(22) Filed: Jan. 21, 2014

(65) Prior Publication Data
US 2014/0131223 A1 May 15, 2014

Related U.S. Application Data

(62) Division of application No. 13/322,898, filed as application No. PCT/US2010/037101 on Jun. 2, 2010, now Pat. No. 8,668,874.
(Continued)

(51) Int. Cl.
*G01N 15/06* (2006.01)
*G01N 33/00* (2006.01)
(Continued)

(52) U.S. Cl.
CPC ............ *G01N 27/27* (2013.01); *G01N 21/783* (2013.01); *G01N 31/223* (2013.01);
(Continued)

(58) Field of Classification Search
CPC ......... G01N 15/06; G01N 33/00; G01N 33/48
(Continued)

(56) References Cited

U.S. PATENT DOCUMENTS

| 5,958,214 A | 9/1999 | Nikolskaja |
| 6,362,005 B1 | 3/2002 | Tanaka et al. |

(Continued)

FOREIGN PATENT DOCUMENTS

| EP | 2085769 A1 | 8/2009 |
| JP | 0949816 A | 2/1997 |

(Continued)

OTHER PUBLICATIONS

International Search Report, PCT/US2010/037101, Jul. 23, 2010.
(Continued)

*Primary Examiner* — Brian J Sines
(74) *Attorney, Agent, or Firm* — George A. Leone; Citadel Patent Law

(57) ABSTRACT

A gas-phase detection system based on detecting optochemical and optoelectrochemical signals. The sensing platform is particularly powerful for detection of nitrogen oxides at low ppbV concentrations. The optochemical analysis is based on the color development due to a chemical reaction taking place in an optimized material. The electrochemical analysis can be based on the doping level or redox potential changes of an electrochemical sensor; and optoelectrochemical detection can be based on a combination of the electrochemical and optoelectrochemical methodologies. Each independent signal can be simultaneously detected, increasing the reliability of detection.

13 Claims, 4 Drawing Sheets

Related U.S. Application Data

(60) Provisional application No. 61/184,596, filed on Jun. 5, 2009.

(51) Int. Cl.
*G01N 33/48* (2006.01)
*G01N 27/27* (2006.01)
*G01N 21/78* (2006.01)
*G01N 31/22* (2006.01)
*G01N 21/05* (2006.01)

(52) U.S. Cl.
CPC ......... *G01N 33/0037* (2013.01); *G01N 21/05* (2013.01); *Y10T 436/173845* (2015.01)

(58) Field of Classification Search
USPC . 422/50, 68.1, 83, 82.01, 82.02, 98; 436/43, 106, 116, 117, 118
See application file for complete search history.

(56) References Cited

U.S. PATENT DOCUMENTS

| | | | |
|---|---|---|---|
| 6,406,669 | B1 | 6/2002 | Duan et al. |
| 6,703,216 | B2 | 3/2004 | Parsons et al. |
| 7,547,931 | B2* | 6/2009 | Star et al. ............... 257/253 |
| 8,383,412 | B2* | 2/2013 | Zamborini et al. ......... 436/144 |
| 8,668,874 | B2* | 3/2014 | Tao et al. ................. 422/91 |
| 8,754,454 | B2* | 6/2014 | Bryant et al. ............. 257/253 |
| 8,845,880 | B2* | 9/2014 | Davis et al. .............. 205/792 |
| 8,920,619 | B2* | 12/2014 | Salzer et al. ............ 204/403.03 |
| 9,006,796 | B2* | 4/2015 | Occhipinti ............... 257/253 |
| 9,103,775 | B2* | 8/2015 | Bradley et al. |
| 2003/0036202 | A1 | 2/2003 | Teodorcyzk et al. |
| 2003/0040120 | A1 | 2/2003 | Allen et al. |
| 2003/0044316 | A1 | 3/2003 | Hirai et al. |
| 2003/0097981 | A1 | 5/2003 | Dick et al. |
| 2005/0034985 | A1 | 2/2005 | Zamanzadeh et al. |
| 2005/0279995 | A1* | 12/2005 | Shin et al. ............... 257/40 |
| 2006/0036138 | A1 | 2/2006 | Heller et al. |
| 2007/0086920 | A1 | 4/2007 | Anvar et al. |
| 2008/0038820 | A1* | 2/2008 | Rudy-Reil ............... 435/377 |
| 2008/0220984 | A1 | 9/2008 | Bright et al. |
| 2008/0221806 | A1 | 9/2008 | Bryant et al. |
| 2008/0231849 | A1 | 9/2008 | Myrick et al. |
| 2008/0257648 | A1 | 10/2008 | Bohm et al. |

FOREIGN PATENT DOCUMENTS

| | | |
|---|---|---|
| JP | 09274032 A | 10/1997 |
| JP | 2007017317 A | 1/2007 |
| JP | 2008082840 | 4/2008 |
| WO | WO2007047532 A1 | 4/2007 |
| WO | WO2008106412 A1 | 9/2008 |

OTHER PUBLICATIONS

Written Opinion of the International Searching Authority, PCT/US2010/037101, Jul. 23, 2010.
International Preliminary Report on Patentability, PCT/US2010/037101, Dec. 6, 2011.
Notice of Allowance and Fees Due, U.S. Appl. No. 13/322,898, Dec. 4, 2014.
Non-Final Office Action, U.S. Appl. No. 13/322,898, Jun. 12, 2013.
Response to Non-Final Office Action, U.S. Appl. No. 13/322,898, Sep. 9, 2013.
Final Office Action, U.S. Appl. No. 13/322,898, Sep. 24, 2013.
Response to Final Office Action, U.S. Appl. No. 13/322,898, Nov. 20, 2013.
Applicant Initiated Interview Summary, U.S. Appl. No. 13/322,898, Aug. 20, 2013.
Requirement for Restriction/Election, U.S. Appl. No. 13/322,898, Apr. 9, 2013.
Response to Restriction/Election Requirement, U.S. Appl. No. 13/322,898, May 7, 2013.
Extended European Search Report Oct. 28, 2015.

* cited by examiner

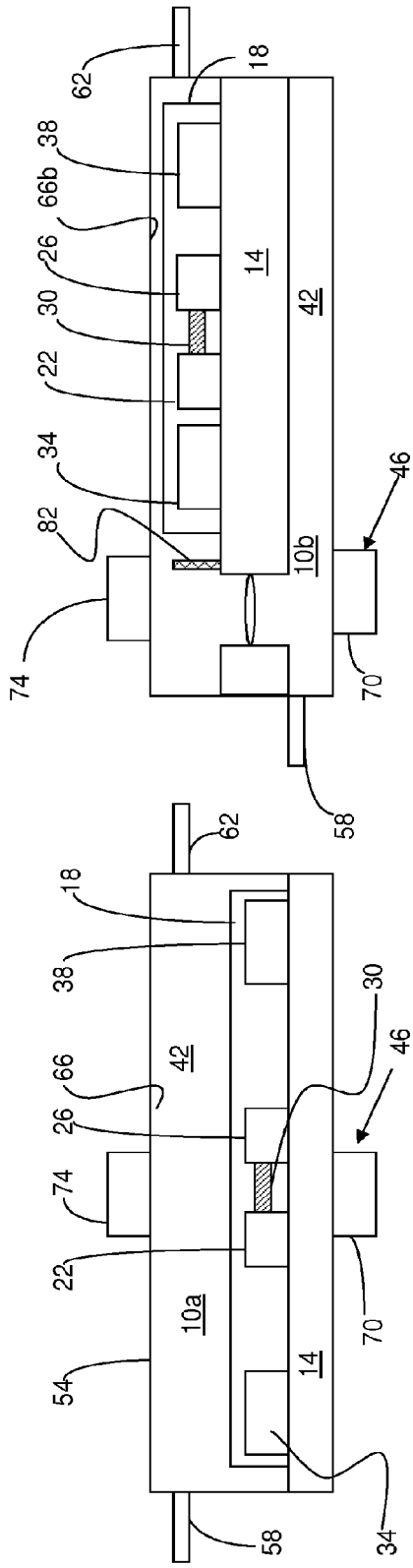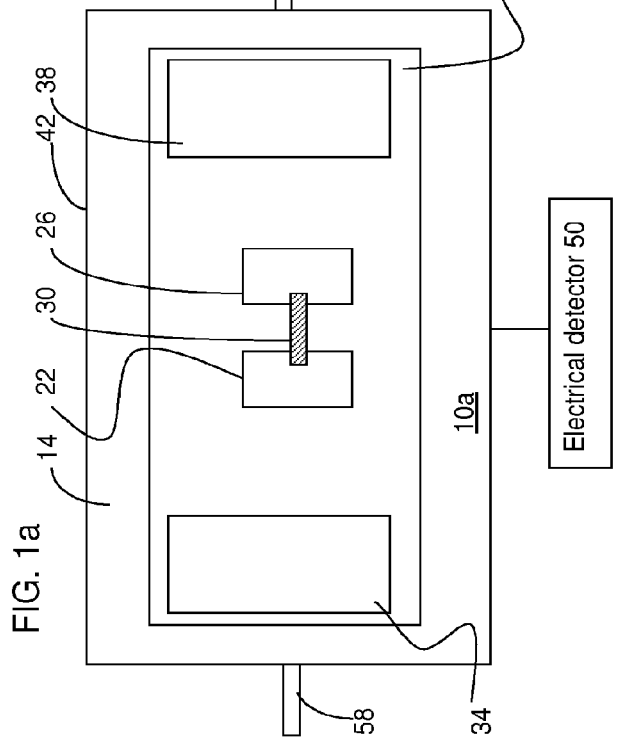

INTEGRATED OPTOELECTROCHEMICAL SENSOR FOR NITROGEN OXIDES IN GASEOUS SAMPLES

RELATED APPLICATION

This application claims priority from and is a divisional of co-pending U.S. application Ser. No. 13/322,898 of Tao, et al., having Section 371(c) filing date Jan. 26, 2012, entitled "INTEGRATED OPTOELECTROCHEMICAL SENSOR FOR NITROGEN OXIDES IN GASEOUS SAMPLES." U.S. application Ser. No. 13/322,898 of Tao, et al., is hereby incorporated by reference.

BACKGROUND OF THE INVENTION

1. Field of the Invention

The present invention relates generally to chemical sensors and, more particularly, to systems and methods for integrated electrochemical, electrical, and/or optical detection.

2. Background Information

Nitrogen oxides (NOx) are important environmental pollutants. Their levels in human breath are also key biomarkers of diseases, such as asthma. Existing methods and devices may detect unknown analytes, but are generally slow, expensive, and/or bulky. Miniaturized sensors and methods generally lack sufficient sensitivity, selectivity, and/or reliability; and may be especially deficient for detecting one or more analytes in complex matrices, such as ambient air or human breath.

SUMMARY

The present disclosure includes chemical sensors and methods for detecting nitrogen oxides based on one or both of two detection principles, optical and electrochemical, that may be combined to improve the selectivity and reliability.

The present sensing devices are capable of detecting nitrogen oxides through the integration of two different principles: electrochemical and optical, capable of reaching low ppbV and ppmV detection limits, respectively. The present devices allow for different alternatives for tuning the system in order to improve the selectivity.

Advantages of the present embodiments of sensors and methods may include: improved selectivity and reliability over previous devices, such as previous devices based on single detection method; real-time detection of the analyte; high capability and/or suitability for integration into other devices, such as portable devices, (e.g., with high throughput fabrication processes); improved reliability of results by decreasing false positive and false negative responses; and/or simultaneous detection of distinctive gases for environmental or biomedical applications.

The present sensors may have applications not only in environmental monitoring, but also as non-invasive medical diagnosis and management devices for asthma and other diseases. The present sensors and/or methods may, for example, be configured and/or used for lab-based analytical devices, handheld or portable chemical sensors and tasks, and/or the like.

Embodiments of the present sensors include integrated sensors or sensor devices that can perform independent or combined electrochemical and/or optical detection of nitrogen and their reaction products. Embodiments of the present sensors and methods integrate electrochemical and/or optical sensing principles into a single device to detect nitrogen oxides, and may thereby exhibit improved selectivity and reliability. The present sensors can be configured in multiple ways, such as, for example, to obtain a combined optoelectrochemical signal, and/or to obtain independent optical and electrochemical signals. Simultaneous detection of nitrogen oxides can be achieved by implementing two or more sensor elements (e.g., in the same compartment, or in different compartments that may be separated by a filter piece). Sensor elements can comprise or be embedded with redox dyes, aromatic diamines, and/or coordination complex probes.

Some embodiments of the present sensors comprise: an aromatic amine compound coupled to the substrate; a gas flow system in fluid communication with the substrate; and an optical detection system configured to detect optical changes of the aromatic amine compound. In some embodiments, the substrate comprises at least one material selected from the group consisting of: cellulose, cellulose derivatives, glass, plastic, metallic mesh, zeolites, silica particles, and alumina particles.

In some embodiments, the substrate comprises a porous membrane where the aromatic amine compound is embedded in the porous membrane. In some embodiments, the porous membrane comprises a cellulose/polyester membrane that includes alumina particles. In some embodiments, the porous membrane defines a sensing area, where the aromatic amine is confined by a material to the porous membrane. In some embodiments, the material comprises polydimethylsiloxane.

In some embodiments, the aromatic amine compound comprises at least one compound selected from the group consisting of: aromatic monoamines, aromatic monoamine derivatives, aromatic diamines, 1,2-diaminobenzene, aromatic diamine derivatives, naphthalenediamines, and naphthalenediamine derivatives.

In some embodiments, the gas flow system comprises an inlet and an outlet. In some embodiments, the gas flow system comprises a filter. In some embodiments, the optical detection system comprises a light source and an optical detector. In some embodiments, the light source and the optical detector are located on the same side of the substrate.

In some embodiments, the substrate comprises a porous membrane. In some embodiments, the light source is located on one side of the porous membrane and the optical detector is located on an opposite side of the porous membrane from the light source.

In some embodiments, the optical detection system comprises an optical waveguide. In some embodiments, the light source comprises a light emitting diode (LED). In some embodiments, the optical detector comprises a charge-coupled device (CCD) camera. In some embodiments, the optical detector is a complementary metal-oxide semiconductor (CMOS) camera.

Some embodiments of the present sensors comprise: a second electrode coupled to the substrate and spaced apart from the first electrode; a coupler coupling the first electrode to the second electrode; an electrolyte coupled to the substrate; a detector substance coupled to the substrate, the detector substance configured to be sensitive to nitrogen oxides; a counter electrode coupled to the substrate; a reference electrode coupled to the substrate; a gas flow system in fluid communication with the substrate; and an electrical detector coupled to at least two of the first electrode, second electrode, counter electrode, and reference electrode, the electrical detector configured to detect electrical changes in the coupler.

In some embodiments, the coupler comprises a conducting or semiconducting material. In some embodiments, the conducting or semiconducting material comprises one or more materials selected from the group consisting of: metal oxides, metal oxide derivatives, polypyrroles, polypyrrole derivatives, polyanilines, polyaniline derivatives, polythiophenes, polythiophene derivatives, and poly(3,4-ethylenedioxythiophene).

In some embodiments, the electrolyte comprises an ionic liquid or a low vapor pressure solvent having an electrolyte. In some embodiments, the detector substance is disposed on the reference electrode. In some embodiments, the detector substance is disposed in the electrolyte. In some embodiments, the detector substance comprises one or more materials selected from the group consisting of: aromatic monoamines, aromatic monoamine derivatives, aromatic diamines, 1,2-diaminobenzene, aromatic diamine derivatives, naphthalenediamines, naphthalenediamine derivatives, hemoproteins, hemopeptides, metal phtalocyanines, metal phtalocyanine derivatives, metal porphyrins, metal porphyrins derivatives, iron (II) carbamates, and iron (II) carbamate derivatives.

In some embodiments, the detector substance is disposed on the reference electrode, where the detector substance comprises one or more materials selected from the group consisting of: silver, aromatic monoamines, aromatic monoamine derivatives, aromatic diamines, 1,2-diaminobenzene, aromatic diamine derivatives, naphthalenediamines, naphthalenediamine derivatives, hemoproteins, hemopeptides, metal phtalocyanines, metal phtalocyanine derivatives, metal porphyrins, metal porphyrin derivatives, iron (II) carbamates, and iron (II) carbamate derivatives.

In some embodiments, the gas flow system comprises an inlet and an outlet. In some embodiments, the gas flow system comprises a filter.

In some embodiments, the electrical detector is configured to control and measure one or more electrical changes of the one or more coupled electrodes. In some embodiments, the electrical detector is coupled to the first electrode, and is configured to provide a potential perturbation. In some embodiments, the electrical detector comprises a bipotentiostat. In some embodiments, the electrical detector is coupled to the first electrode, the second electrode, and the reference electrode, and the electrical detector is configured to measure one or more electrical changes and/or properties selected from the group consisting of potential shift, conductance, and electrical current.

In some embodiments, the detector substance is mixed into the electrolyte, and where the sensor is configured such that if one or more nitrogen oxides are introduced to the electrolyte, the detector substance will chemically react with at least one of the one or more nitrogen oxides and the one or more electrical changes can be measured simultaneously with the chemical reaction. In some embodiments, the detector substance is disposed on the reference electrode, where the sensor is configured such that if one or more nitrogen oxides are introduced to the reference electrode, the detector substance will chemically react with at least one of the one or more nitrogen oxides and the one or more electrical changes can be measured simultaneously with the chemical reaction.

Some embodiments of the present sensors comprise: a substrate; an aromatic amine compound coupled to the substrate; a first electrode coupled to the substrate; a second electrode coupled to the substrate and spaced apart from the first electrode; a coupler coupling the first electrode to the second electrode; an electrolyte coupled to the substrate; a detector substance coupled to the substrate, the detector substance configured to be sensitive to nitrogen oxides; a counter electrode coupled to the substrate; a reference electrode coupled to the substrate; a gas flow system in fluid communication with the substrate; an optical detection system configured to detect optical changes of the aromatic amine compound; and an electrical detector coupled to at least two of the first electrode, second electrode, counter electrode, and reference electrode, the electrical detector configured to detect one or more electrical changes in the coupler.

Some embodiments of the present methods comprise: providing a sensor (the sensor comprising: a substrate; an aromatic amine compound coupled to the substrate; and an optical detection system configured to detect optical changes of the aromatic amine compound); directing a sample containing at least one nitrogen oxide to be in fluid communication with the substrate such that the at least one nitrogen oxide chemically reacts with the aromatic amine compound coupled to the substrate; detecting a reaction product of the chemical reaction; detecting with the optical detection system an optical change of the aromatic amine compound; and detecting the at least one nitrogen oxide from the optical change.

In some embodiments, the substrate comprises a porous membrane, the aromatic amine compound is embedded in the porous membrane, and directing a sample comprises directing a sample to be in fluid communication with the porous membrane. In some embodiments, directing a sample comprises directing a sample through the porous membrane. In some embodiments, the optical detection system of the sensor comprises a light source and an optical detector, and where detecting with the optical detection system comprises transmitting light with the light source from a first side of the porous membrane through the porous membrane and receiving at least a portion of the transmitted light with the optical detector on an opposite side of the porous membrane.

In some embodiments, the optical detection system of the sensor comprises a light source and an optical detector, where detecting with the optical detection system comprises transmitting light with the light source from a first side of the porous membrane such that at least a portion of the light is reflected by the porous membrane and receiving the at least a portion of the reflected light with the optical detector on the same first side of the porous membrane. In some embodiments, the optical detection system of the sensor comprises a light source and an optical detector, where the optical detector is configured to receive light via a waveguide.

Some embodiments of the present methods comprise: providing a sensor (the sensor comprising: a first electrode coupled to a substrate; a second electrode coupled to the substrate and spaced apart from the first electrode; a coupler coupling the first electrode to the second electrode; an electrolyte coupled to the substrate; a detector substance coupled to the substrate, the detector substance configured to be sensitive to nitrogen oxides; a counter electrode coupled to the substrate; a reference electrode coupled to the substrate; and an electrical detector coupled to at least two of the first electrode, second electrode, counter electrode, and reference electrode, the electrical detector configured to detect electrical changes in the coupler); directing a sample containing at least one nitrogen oxide to be in fluid communication with the substrate such that the at least one nitrogen oxide chemically reacts with the detector substance coupled to the substrate; detecting a reaction product of the chemical reaction; detecting with the electrical detector an electrical change of the coupler; and detecting the at least one nitrogen oxide from the electrical change.

In some embodiments, the detector substance is disposed in the electrolyte such that the reaction product is formed in the electrolyte. In some embodiments, the detector substance is disposed on the reference electrode such that the reaction product is formed on the reference electrode.

Some embodiments of the present methods comprise: providing a sensor (the sensor comprising: a substrate; an aromatic amine compound coupled to the substrate; a first electrode coupled to the substrate; a second electrode coupled to the substrate and spaced apart from the first electrode; a coupler coupling the first electrode to the second electrode; an electrolyte coupled to the substrate; a detector substance coupled to the substrate, the detector substance configured to be sensitive to nitrogen oxides; a counter electrode coupled to the substrate; a reference electrode coupled to the substrate; a gas flow system in fluid communication with the substrate; an optical detection system configured to detect optical changes of the aromatic amine compound; and an electrical detector coupled to at least two of the first electrode, second electrode, counter electrode, and reference electrode, the electrical detector configured to detect one or more electrical changes in the coupler); directing a sample containing at least one nitrogen oxide to be in fluid communication with the substrate such that the at least one nitrogen oxide chemically reacts with the aromatic amine compound and the detector substance; detecting a reaction product of at least one of the chemical reactions; detecting with the optical detection system an optical change of the aromatic amine compound; detecting with the electrical detector an electrical change of the coupler; and detecting the at least one nitrogen oxide from at least one of the optical change and the electrical change.

Any embodiment of any of the present methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Details associated with the embodiments described above and others are presented below.

BRIEF DESCRIPTION OF THE FIGURES

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 1a-1d Schematic representations of two embodiments of the present sensors: FIG. 1a and FIG. 1c show Embodiment 1 and FIG. 1b and FIG. 1d show Embodiment 2.

DESCRIPTION OF ILLUSTRATIVE EMBODIMENTS

Figure 2:
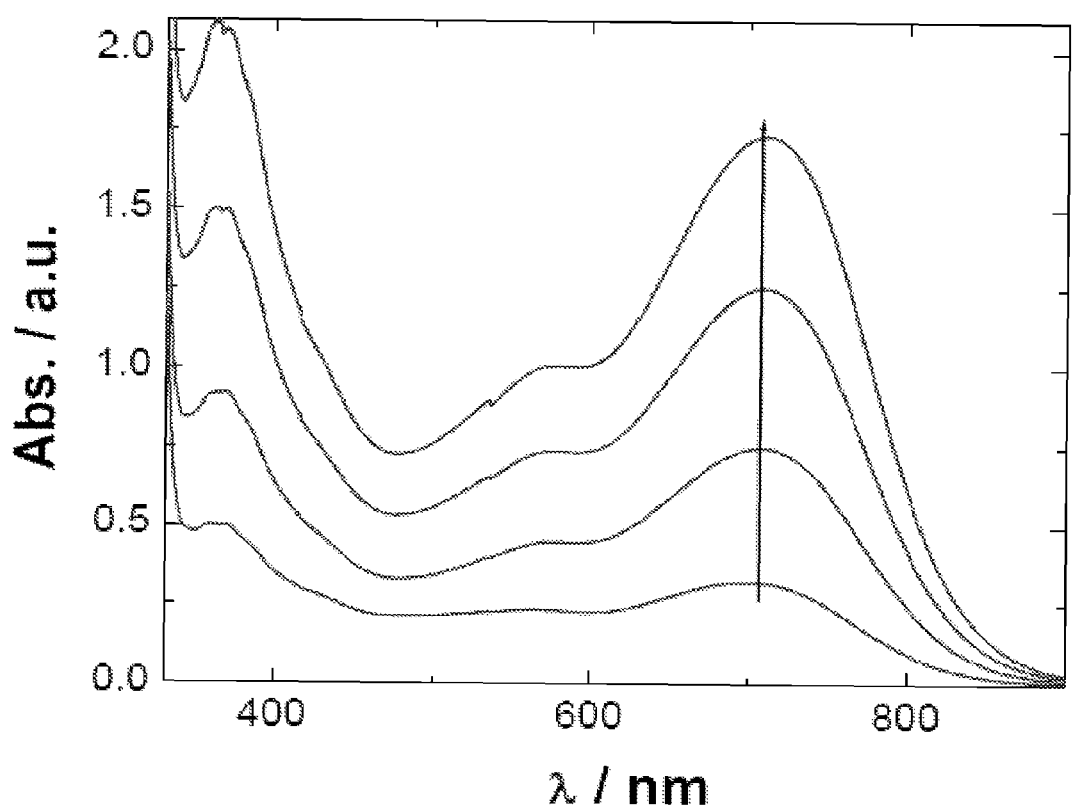
FIG. 2 Spectra corresponding to the product formation during the reaction of nitrogen oxides with 1,2-diaminobenzene (PDA) dissolved in acetonitrile. Bubbling rate=20 mL·min$^{-1}$. Concentration of NOx ($C_{NOx}$)=0.50 ppmV, Concentration of PDA=5 mM. Spectra taken every 2 minutes.

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps (e.g., may possess additional steps).

Further, a device or structure that is configured in a certain way is configured in at least that way, but it can also be configured in other ways than those specifically described.

Referring now to the drawings, and more particularly to FIG. 1a-FIG. 1d, two embodiments are shown of the present sensors. FIG. 1a and FIG. 1c depict top and side cross-sectional views of a first embodiment 10a of an optoelectrical sensor. FIG. 1b and FIG. 1d depict top and side cross-sectional views of a second embodiment 10b of an optoelectrical sensor. Similar elements between embodiments 10a and 10b are labeled with similar reference numerals; however, it should be understood that such elements are not necessarily identical between the two embodiments and may instead vary in position and/or configuration.

Sensor 10a comprises a substrate 14, an electrolyte 18 coupled to the substrate; a chemical probe (e.g., an aromatic amine compound) coupled to the substrate (e.g., mixed into or embedded in electrolyte and coupled to the substrate by way of the electrolyte); two (first and second) working electrodes (WE1 and WE2) 22 and 26 coupled to the substrate and spaced apart from one another (e.g., first electrode 22 and second electrode 26 spaced apart from first electrode 22), a coupler 30 coupling first electrode 22 to second electrode 26; and a detector substance coupled to the substrate (e.g., mixed into or embedded in electrolyte and coupled to the substrate by way of the electrolyte). In various embodiments, the detector substance can be configured to be sensitive to at least one nitrogen oxide.

The substrate can, for example, comprise any suitable material and can be opaque, translucent, and/or transparent. In some embodiments, the substrate comprises at least one material selected from the group consisting of: cellulose, cellulose derivatives, glass, plastic, metallic mesh, zeolites, silica particles, sol-gel, and alumina particles. The electrolyte can be a liquid, solid or semisolid, such as, for example, an ionic liquid, a low vapor pressure solvent having an electrolyte, and/or the like. Ionic liquids may provide thermal and lifetime stability, selectivity towards the analyte and preconcentration capability. The chemical probe or aromatic amine compound can be configured to change color and/or to produce a change in color in or with the electrolyte in the presence of an analyte such as, for example, nitrogen dioxide, and/or the like (e.g., if a gaseous sample comprising an appropriate analyte is placed in fluid communication with the substrate (e.g., in fluid communication with the aromatic amine compound, such as, for example, via the electrolyte). In some embodiments, the aromatic amine compound comprises at least one compound selected from the group consisting of: aromatic monoamines, aromatic monoamine derivatives, aromatic diamines, 1,2-diaminobenzene, aromatic diamine derivatives, naphthalenediamines, and naphthalenediamine derivatives.

The detector substance can, for example, comprise one or more materials selected from the group consisting of: aromatic monoamines, aromatic monoamine derivatives, aromatic diamines, 1,2-diaminobenzene, aromatic diamine derivatives, naphthalenediamines, naphthalenediamine derivatives, hemoproteins, hemopeptides, metal phtalocyanines, metal phtalocyanine derivatives, metal porphyrins, metal porphyrins derivatives, iron (II) carbamates, and iron (II) carbamate derivatives. Coupler 30 can comprise, for example, one or more conducting or semiconducting materials. In some embodiments, for example, the one or more conducting or semiconducting materials are selected from the group consisting of: metal oxides, metal oxide derivatives, polypyrroles, polypyrrole derivatives, polyanilines, polyaniline derivatives, polythiophenes, polythiophene derivatives, and poly(3,4-ethylenedioxythiophene). In embodiments where the detector substance is mixed into or embedded in the electrolyte, the sensor can be configured such that if one or more (e.g., one, two, three, four, five, six, seven, eight, nine, ten, or more) nitrogen oxides are introduced to the electrolyte (e.g., in a gas that is directed in fluid communication with the electrolyte, the detector substance will chemically react with at least one of the one (e.g., one, two, three, four, five, six, seven, eight, nine, ten, or more) or more nitrogen oxides and the one or more electrical properties and/or changes (e.g., of coupler 30) can be measured simultaneously with the chemical reaction.

Sensor 10a further comprises a counter electrode 34 coupled to the substrate; a reference electrode 38 coupled to the substrate; a gas flow system 42 in fluid communication with the substrate; an optical detection system 46 configured to detect optical changes of the aromatic amine compound; and an electrical detector 50 coupled to at least two (e.g., two or more, up to all) of first electrode 18, second electrode 22, counter electrode 34, and reference electrode 38. The electrical detector 50 is configured to detect one or more electrical changes in coupler 30 (e.g., is coupled to first electrode 22 and/or second electrode 26 such that electrical detector 50 is in electrical communication with coupler 30 via first electrode 22 and/or second electrode 26).

In some embodiments, the detector substance is disposed on reference electrode 38 (e.g., coupled to the substrate via reference electrode 38). In embodiment where the detector substance is disposed on the reference electrode, the detector substance can, for example, comprise one or more materials selected from the group consisting of: silver, aromatic monoamines, aromatic monoamine derivatives, aromatic diamines, 1,2-diaminobenzene, aromatic diamine derivatives, naphthalenediamines, naphthalenediamine derivatives, hemoproteins, hemopeptides, metal phtalocyanines, metal phtalocyanine derivatives, metal porphyrins, metal porphyrin derivatives, iron (II) carbamates, and iron (II) carbamate derivatives. In embodiments where the detector substance is disposed on the reference electrode, the sensor can be configured such that if one or more nitrogen oxides are introduced to the reference electrode (e.g., in a gas that is directed in fluid communication with, around, or in contact with the electrode, the detector substance will chemically react with at least one of the one or more nitrogen oxides and the one or more electrical properties and/or changes (e.g., of coupler 30) can be measured simultaneously with the chemical reaction.

Gas flow system 42 comprises a housing 54 having an inlet 58 and an outlet 62. Housing 54 cooperates with substrate 14 to define a sample chamber 66 through which a gas or fluidic sample can pass or be directed in fluid communication with the substrate (e.g., with the electrolyte and/or the aromatic amine compound). In this way, gas flow system 42 is in fluid communication with the substrate (e.g., a gas or other fluid disposed and/or flowing through gas flow system 42 can be directed in fluid communication with the substrate and any materials on the substrate, such as, for example, electrolyte, chemical probe, and/or the like).

First and second working electrodes (WE1 and WE2) 22 and 26, and coupler, form a conducting junction (e.g., a conducting polymer junction), and electrical detector 50 is configured to measure one or more electrical changes (e.g., conductance, electrochemical potential shift, and/or the like) in coupler 30. In some embodiments, electrical detector 50 is configured to control and/or measure one or more electrical properties and/or changes. For example, in some embodiments, the electrical detector comprises a potentiostat (e.g., a bipotentiostat) that is configured to control the potentials of first and second electrodes 22 and 26 with respect to reference electrode 38 such that current can be allowed to flow between working electrodes 22 and 26 and counter electrode 34. In some embodiments, the electrical detector is configured to provide a potential perturbation.

As noted above, optical detection system 46 is configured to detect optical changes of the aromatic amine compound (e.g., optical changes in the electrolyte due to chemical reaction of an analyte with the aromatic amine compound, such as, for example, at and/or near first electrode 22, second electrode 26, and/or junction 30. Optical detection system 46 comprises a light source 70 and optical detector 74 (photodetector or camera). In the embodiment shown, light source 70 is disposed on a first side of the substrate and an optical detector 74 is disposed on an opposite side of the substrate, such that if light source 70 is activated to emit otherwise provide light, at least a portion of the light will pass or be transmitted through the substrate and will be received or detected by the optical detector 74 on the opposite side of the substrate. This may be considered a "transmission configuration" in which light is transmitted through the substrate. In other embodiments, the optical detection system may have a "reflection configuration" in which the light source and the optical detector are disposed on the same side of the substrate, such that if the light source is activate to provide light, at least some portion (up to all) of the light will be reflected away from the substrate and received by the optical detector on the same side of the substrate. In some embodiments, light detection system 46 comprises one or more optical waveguide (not shown) that may, for example, be integrated into the light source and/or the optical detector.

The light source can comprise any suitable light source, such as, for example, a white light source, a light emitting diode (LED), or the like. In some embodiments, it may be desirable that the light source has an emission (provides light) in a certain region of the visible spectrum, such as, for example, an LED with a known spectral distribution, or a broader-band light source coupled with band-pass filters in order to give a narrower emission band, such that the selectivity of the optical detection of the sensor may be improved. The optical detector can comprise: a charge-coupled device (CCD) camera, a complementary metal-oxide semiconductor (CMOS) camera, and/or the like. In some embodiments, a webcam or filter-modified photodiode arrays may be advantageous to increase and/or match the selectivity that may be provided or enabled by narrow or controlled-band light source.

Junction 30 comprises a conductive or semiconductive material (e.g., a polymer, a metal, and/or the like), deposited and/or disposed between first electrode 22 and second electrode 26 to form a conduction pathway between first and second electrodes 22 and 26. Junction 30 is configured to be used in an electrochemical transistor configuration where first and second electrodes 22 and 26 are the source and the drain electrodes, and a gate potential ($V_g$) is applied via reference electrode 38, together with counter electrode 34, and the electrical detector 50 (e.g., a potentiostat). The electrical detector (and/or detection system) is configured to monitor and/or permit a user to monitor the source-drain current ($I_{sd}$), such as with a bias voltage ($V_{bias}$) between first and second electrodes 22 and 36 at various gate potential values, $V_g$.

When nitrogen oxides are dissolved in the electrolyte (e.g., via a gaseous or fluidic sample in fluid communication with the electrolyte), either a change in the conductance (doping level) of the conducting polymer junction or a change in the electrochemical potential in electrolyte 18 and reference electrode 38 may be produced by the analyte itself or by reaction products. In addition, optical changes (e.g., changes in color) can be recorded or registered using the light source and photodetector as described above.

As shown in FIG. 1(b), sensor 10b is similar in some respects to sensor 10a. For example, sensor 10b comprises a substrate 14; an aromatic amine compound coupled to substrate 14; a gas flow system 42 in fluid communication with substrate 14; and an optical detection system 42 configured to detect optical changes of the aromatic amine compound. However, sensor 10b comprises a porous membrane 78 and the aromatic amine compound (or probe, described above) can be embedded in porous membrane 78 which may be referred to as a sensing region (e.g., optical sensing region). In some embodiments, porous membrane 78 is partially (up to fully) saturated with the aromatic amine compound. Porous membrane 78 can, for example, comprise a cellulose/polyester membrane (e.g., that can include alumina particles for reinforcement or the like). In some embodiments, the aromatic amine is confined to the sensing region by a material (e.g., polydimethylsiloxane). As shown, sensor 10b also comprises an optical detection system 46 having a light source 70 located on one side of the porous membrane and an optical detector 74 located on an opposite side of the porous membrane from the light source.

Sensor 10b also comprises: a first electrode 22 coupled to the substrate; a second electrode 26 coupled to the substrate and spaced apart from the first electrode; a coupler 30 coupling the first electrode to the second electrode; an electrolyte 18 coupled to the substrate; a detector substance coupled to the substrate and configured to be sensitive to nitrogen oxides; a counter electrode 34 coupled to the substrate; a reference electrode 38 coupled to the substrate; a gas flow system 42 in fluid communication with the substrate; and an electrical detector 50 coupled to at least two of the first electrode, second electrode, counter electrode, and reference electrode, the electrical detector configured to detect electrical changes in the coupler.

Sensor 10b is also somewhat different in that gas flow system 42 comprises a filter 82 between the optical sensing region and the remainder of the substrate (the portions used for electrochemical sensing). Housing 54 of sensor 10b can define cavities 66a and 66b on both sides of substrate 14 (and in fluid communication with one another via porous substrate 78), such that gas inlet 58 enters cavity 66a and gas outlet 62 exits cavity 66b. In this way, gas can be directed through gas inlet 58 into cavity 66a, through porous substrate 78 into cavity 66b, and out of cavity 66b via gas outlet 62. As discussed above, in embodiments of the present sensors can have a cavity on only one side of the substrate with a gas inlet and gas outlet both on a single side of the substrate.

The separation of optical and electrochemical sensing regions in sensor 10b permits detection and/or identification of nitrogen oxides in two independent ways using two different detection principles. In this way, the selectivity of sensor 10b can be "tuned up" or improved by using different chemical reactions for each one of the sensing elements. In the embodiment shown, sensor 10b is an integrated sensor that includes both optical and electrochemical detection functions. In other embodiments, the sensor can include only the optical portion or only the electrochemical portion.

The present disclosure further includes methods of using various embodiments of the present sensors. For example, in one example of a method of using a sensor having an optical detection portion, the method comprises: providing a sensor that comprises a substrate (e.g., 14), an aromatic amine compound coupled to the substrate, and an optical detection system (e.g., 46) configured to detect optical changes of the aromatic amine compound. The method can further comprise directing (e.g., via a gas flow system 42) a sample containing at least one nitrogen oxide to be in fluid communication with the substrate such that the at least one nitrogen oxide chemically reacts with the aromatic amine compound coupled to the substrate; detecting a reaction product of the chemical reaction; detecting with the optical detection system an optical change (e.g., a change in color, reflection spectrum, transmission spectrum, and/or the like) of the aromatic amine compound; and detecting (e.g., identifying) the at least one nitrogen oxide from the optical change. In some embodiments, the substrate comprises a porous membrane (e.g., 78), the aromatic amine compound is embedded in the porous membrane, and directing a sample comprises directing a sample to be in fluid communication with the porous membrane. In some embodiments, directing a sample comprises directing a sample through the porous membrane (e.g., as described above for sensor 10b).

In some embodiments of this method, the optical detection system of the sensor comprises a light source and an optical detector, and detecting with the optical detection system comprises transmitting light with the light source from a first side of the porous membrane through the porous membrane and receiving at least a portion of the transmitted light with the optical detector on an opposite side of the porous membrane (e.g., as described above for sensor 10b). In other embodiments, detecting with the optical detection system comprises transmitting light with the light source from a first side of the porous membrane such that at least a portion of the light is reflected by the porous membrane and receiving the at least a portion of the reflected light with the optical detector on the same first side of the porous membrane. In some embodiments, the optical detector is configured to receive light via a waveguide.

In another example of a method of using a sensor having an electrochemical sensing portion, the method comprises providing a sensor that comprises: a first electrode (e.g., 22) coupled to a substrate (e.g., 14); a second electrode (e.g., 26) coupled to the substrate and spaced apart from the first electrode; a coupler (e.g., 30) coupling the first electrode to the second electrode; an electrolyte (e.g., 18) coupled to the substrate; a detector substance coupled to the substrate, the detector substance configured to be sensitive to nitrogen oxides; a counter electrode (e.g., 34) coupled to the substrate; a reference electrode (e.g., 38) coupled to the substrate; and an electrical detector (e.g., 50) coupled to at least two of the first electrode, second electrode, counter electrode, and reference electrode, the electrical detector configured to detect electrical changes in the coupler. The method can further comprise directing (e.g., via a gas flow system 42) a sample containing at least one nitrogen oxide to be in fluid communication with the substrate such that the at least one nitrogen oxide chemically reacts with the detector substance coupled to the substrate; detecting a reaction product of the chemical reaction; detecting with the electrical detector an electrical change of the coupler; and detecting the at least one nitrogen oxide from the electrical change. In some embodiments, the detector substance is disposed in the electrolyte such that the reaction product is formed in the electrolyte. In other embodiments, the detector substance is disposed on the reference electrode such that the reaction product is formed on the reference electrode.

In another example of a method of using an integrated sensor having both optical and electrochemical sensing portions, the method comprises providing a sensor that comprises: a substrate (e.g., 14); an aromatic amine compound coupled to the substrate; a first electrode (e.g., 22) coupled to the substrate; a second electrode (e.g., 26) coupled to the substrate and spaced apart from the first electrode; a coupler (e.g., 30) coupling the first electrode to the second electrode; an electrolyte (e.g., 18) coupled to the substrate; a detector substance coupled to the substrate, the detector substance configured to be sensitive to nitrogen oxides; a counter electrode (e.g., 34) coupled to the substrate; a reference electrode (e.g., 38) coupled to the substrate; a gas flow system (e.g., 42) in fluid communication with the substrate; an optical detection system (e.g., 46) configured to detect optical changes of the aromatic amine compound; and an electrical detector (e.g., 50) coupled to at least two of the first electrode, second electrode, counter electrode, and reference electrode, the electrical detector configured to detect one or more electrical changes in the coupler. The method can further comprise directing (e.g., via gas flow system 42) a sample containing at least one nitrogen oxide to be in fluid communication with the substrate such that the at least one nitrogen oxide chemically reacts with the aromatic amine compound and the detector substance; detecting a reaction product of at least one of the chemical reactions; detecting with the optical detection system an optical change of the aromatic amine compound; detecting with the electrical detector an electrical change of the coupler; and detecting the at least one nitrogen oxide from at least one of the optical change and the electrical change.

EXAMPLES AND EXPERIMENTAL DATA

1. Part-Per-Billion (ppbV) Detection Level of Nitrogen Oxides (NOx) Using Optical Detection A. Nitrogen Oxides Bubbled in 1,2-Diaminobenzene/Acetonitrile Solution Nitrogen oxides, diluted in air, were bubbled in a 1,2-diaminobenzene/acetonitrile solution and visible absorption spectra obtained. When nitrogen oxides, diluted in air, are flowing through an acetonitrile solution of 1,2-diaminobenzene, a strong color-development was observed in the solution.

FIG. 2 shows the corresponding visible absorption spectra in which the main visible absorption band is located at around 700 nm with a shoulder at a lower wavelength around 580 nm. Another strong band developed at 350 nm. The high value of the molar absorptivity allows for the detection of very low concentrations of nitrogen oxides. Additionally, the multi-band absorption spectrum allows for improvement of the selectivity of the deployed sensor through optimization of the light source emission.

B. Flow of Nitrogen Oxides Through White Cloth with 1,2-Diaminobenzene

Nitrogen oxides were directed through a white cloth embedded with 1,2-diaminobenzene: the reaction between nitrogen oxides and 1,2-diaminobenzene also takes place in solid phase without any additive or medium control. When nitrogen oxides were forced to flow through a cotton white piece of cloth saturated with solid 1,2-diaminobenzene a color development was also observed.

Figure 3:
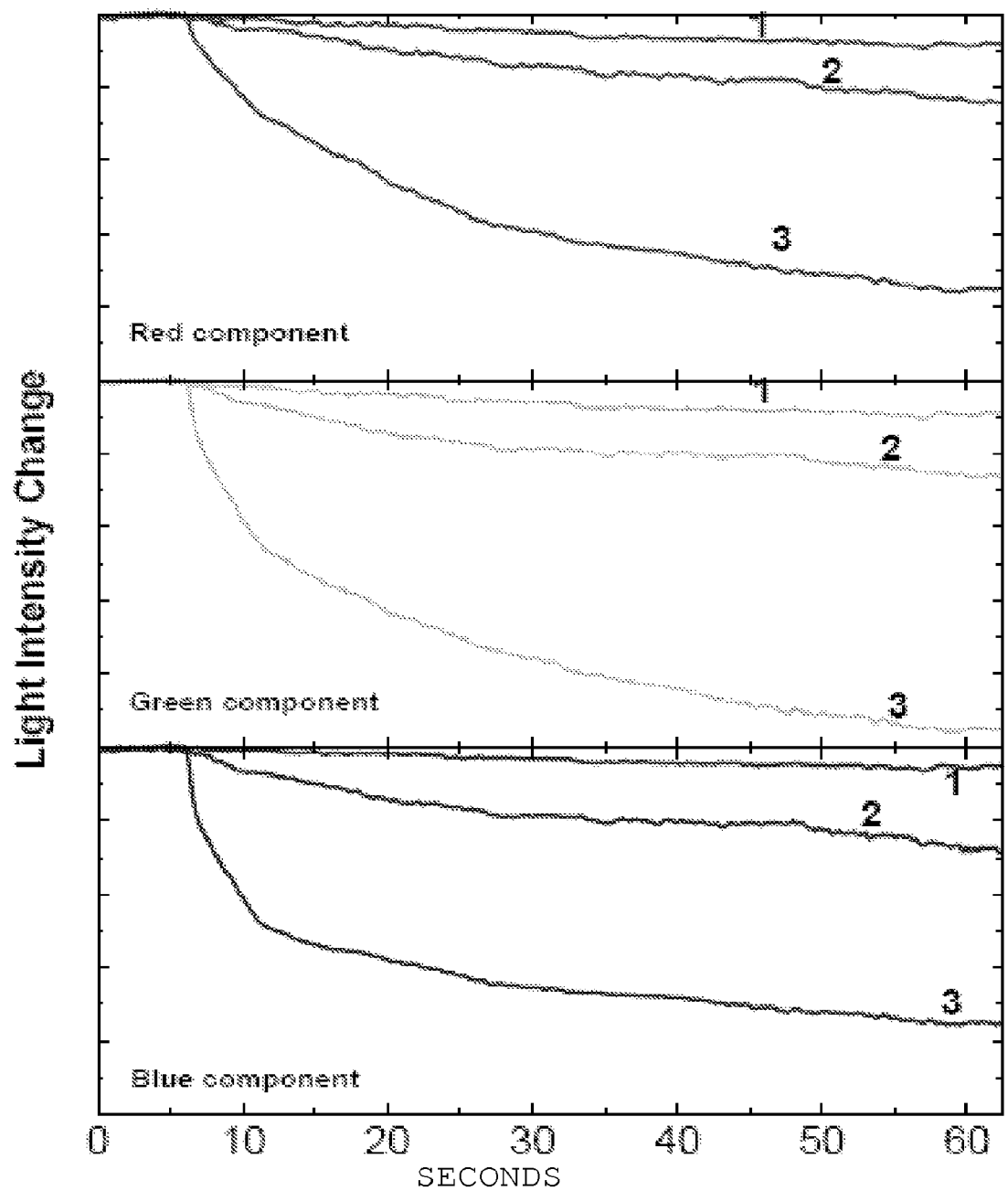
FIG. 3 Red, Green, and Blue (RGB) intensity change cause by reaction between nitrogen oxides and 1,2-diaminobenzene in solid phase. Flow rate=200 mL·min$^{-1}$. Concentration of NOx=0.20 ppmV (1); Concentration of NOx=2.00 ppmV (2); Concentration of NOx=69.0 ppmV (3).

FIG. 3 shows the change of the red, green, and blue (RGB) light components of a white LED light source coming through a piece of cloth embedded with solid 1,2-diaminobenzene during the flow of nitrogen oxides. It can be noted that the response time to reach a steady state signal is only 60 seconds, almost independent of the concentration of nitrogen oxides. The estimated detection limit using the green component is less than 20 ppbV (three times the noise level).

Figure 4:
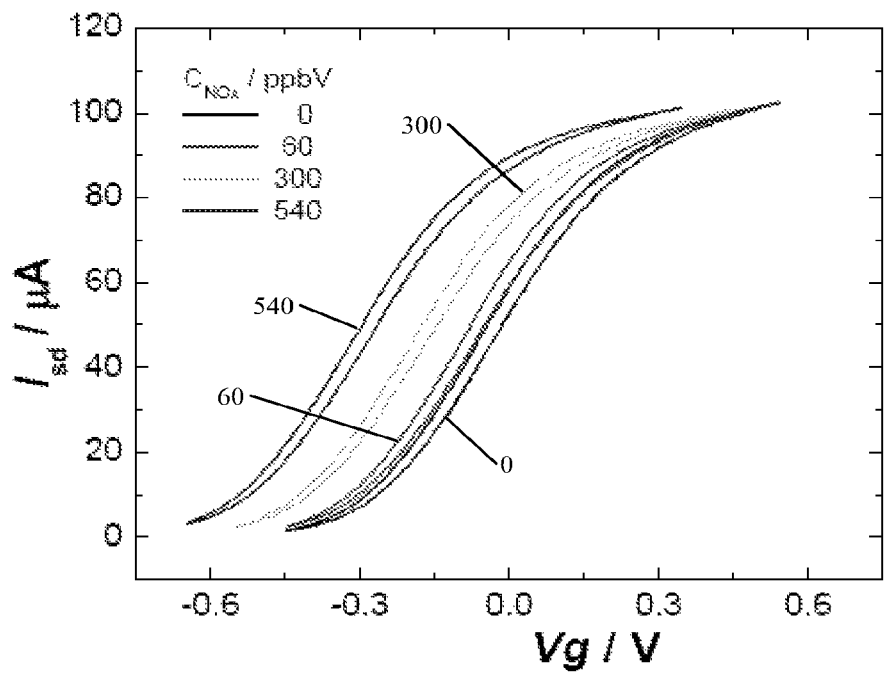
FIG. 4 Potential shift of the source drain current ($I_{sd}$) as a consequence of partition of nitrogen oxides in the ionic liquid electrolyte layer.
Figure 5:
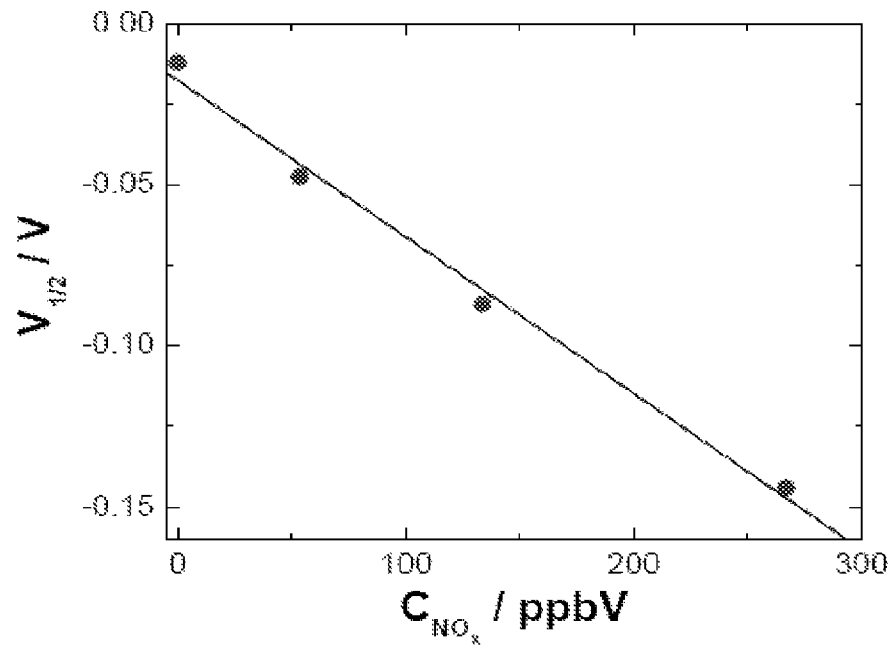
FIG. 5 Calibration plot. Potential shift of source drain current ($I_{sd}$) at half of maximum current ($V_{1/2}$) as a function of the nitrogen dioxide in gas phase.

2. Part-Per-Billion Detection Level of NOx Using Electrochemical Sensors Based on Polymer Nanojunctions FIG. 4 shows several source drain current ($I_{sd}$) profiles corresponding to a polymer nanojunction of poly(3,4-ethylenedioxythiophene) (PEDOT) electropolimerized between two gold microelectrodes (WE1 and WE1) in junction configuration similar to that described above for sensors 10a and 10b. The change of the $I_{sd}$–$V_g$ dependence is likely due to either a change of the doping level of the polymer nanojunction or electrochemical potential of the electrolyte and reference electrode produced by electro-oxidation. This electrochemical experiment was carried out using the ionic liquid 1-butyl 3-methylimidazolium hexafluorophosphate ([bmim] [PF6]) as electrolyte. When nitrogen oxide vapors at very low concentration (ppbV levels) are forced to flow on top of the ionic liquid layer, the $I_{sd}$–$V_g$ profile begins to shift to lower gate potentials, which likely defines either an $I_{sd}$ change at a given $V_g$ or a potential shift at a given $I_{sd}$ that shows a linear dependence with the nitrogen oxide concentration (FIG. 5) that should permit an estimated detection limit of less than 50 ppbV and a very broad dynamic range.

All of the sensors and/or methods disclosed and claimed herein can be made and executed without undue experimentation in light of the present disclosure. While the sensors and methods of this invention have been described in terms of some embodiments, it will be apparent to those of skill in the art that variations may be applied to the sensors and methods and in the steps or in the sequence of steps of the method described herein without departing from the concept, spirit and scope of the invention.

The various illustrative devices, systems, and methods described herein are not intended to be limited to the particular forms disclosed. Rather, they include all modifications, equivalents, and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. A sensor comprising:
   a first electrode coupled to a substrate;
   a second electrode coupled to the substrate and spaced apart from the first electrode;
   a coupler consisting solely of poly(3,4-ethylenedioxythiophene), the coupler coupling the first electrode to the second electrode;
   an ionic liquid electrolyte coupled to the substrate;
   a detector substance coupled to the substrate, the detector substance configured to be sensitive to nitrogen oxides;
   a counter electrode coupled to the substrate;
   a reference electrode coupled to the substrate;
   a gas flow system in fluid communication with the substrate; and
   an electrical detector coupled to at least two of the first electrode, second electrode, counter electrode, and reference electrode, the electrical detector configured to detect electrical changes in the coupler.

2. The sensor of claim 1, where the detector substance is disposed on the reference electrode.

3. The sensor of claim 1, where the detector substance is disposed in the electrolyte.

4. The sensor of claim 1, where the detector substance comprises one or more materials selected from the group consisting of: aromatic monoamines, aromatic monoamine derivatives, aromatic diamines, 1,2-diaminobenzene, aromatic diamine derivatives, naphthalenediamines, naphthalenediamine derivatives, hemoproteins, hemopeptides, metal phtalocyanines, metal phtalocyanine derivatives, metal porphyrins, metal porphyrins derivatives, iron carbamates, and iron carbamate derivatives.

5. The sensor of claim 1, where the detector substance is disposed on the reference electrode, and where the detector substance comprises one or more materials selected from the group consisting of: silver, aromatic monoamines, aromatic monoamine derivatives, aromatic diamines, 1,2-diaminobenzene, aromatic diamine derivatives, naphthalenediamines, naphthalenediamine derivatives, hemoproteins, hemopeptides, metal phtalocyanines, metal phtalocyanine derivatives, metal porphyrins, metal porphyrin derivatives, iron carbamates, and iron carbamate derivatives.

6. The sensor of claim 1, where the gas flow system comprises an inlet and an outlet.

7. The sensor of claim 1, where the gas flow system comprises a filter.

8. The sensor of claim 1, where the electrical detector is configured to control and measure one or more electrical changes of the one or more coupled electrodes.

9. The sensor of claim 8, where the electrical detector is coupled to at least the first electrode, and where the electrical detector is configured to provide a potential perturbation.

10. The sensor of claim 8, where the electrical detector comprises a bipotentiostat.

11. The sensor of claim 1, where the electrical detector is coupled to the first electrode, the second electrode, and the reference electrode, and where the electrical detector is configured to measure one or more electrical changes selected from the group consisting of potential shift, conductance, and electrical current.

12. The sensor of claim 11, where the detector substance is mixed into the electrolyte, and where the sensor is configured such that if one or more nitrogen oxides are introduced to the electrolyte, the detector substance will chemically react with at least one of the one or more nitrogen oxides and the one or more electrical changes can be measured simultaneously with the chemical reaction.

13. The sensor of claim 11, where the detector substance is disposed on the reference electrode, and where the sensor is configured such that if one or more nitrogen oxides are introduced to the reference electrode, the detector substance will chemically react with at least one of the one or more nitrogen oxides and the one or more electrical changes can be measured simultaneously with the chemical reaction.

* * * * *